United States Patent
Struck et al.

(10) Patent No.: US 9,952,229 B2
(45) Date of Patent: Apr. 24, 2018

(54) ARGININE VASOPRESSIN PRO-HORMONE AS PREDICTIVE BIOMARKER FOR DIABETES

(71) Applicants: B.R.A.H.M.S GMBH, Hennigsdorf (DE); The General Hospital Corporation, Boston, MA (US)

(72) Inventors: Joachim Struck, Berlin (DE); Andreas Bergmann, Berlin (DE); Olle Melander, Malmo (DE); Christopher Newton-Cheh, Boston, MA (US); Thomas Wang, Boston, MA (US)

(73) Assignees: B.R.A.H.M.S. GmbH, Hennigsdorg (DE); The General Hospital Corporation, Boston, MA (US)

( * ) Notice: Subject to any disclaimer, the term of this patent is extended or adjusted under 35 U.S.C. 154(b) by 0 days.

(21) Appl. No.: 14/750,201

(22) Filed: Jun. 25, 2015

(65) Prior Publication Data
US 2015/0293127 A1 Oct. 15, 2015

Related U.S. Application Data

(62) Division of application No. 13/126,798, filed as application No. PCT/EP2009/007923 on Oct. 29, 2009, now Pat. No. 9,116,153.

(30) Foreign Application Priority Data

Oct. 31, 2008 (EP) .................... 08168096

(51) Int. Cl.
| | | |
|---|---|---|
| G01N 31/00 | (2006.01) | |
| G01N 33/53 | (2006.01) | |
| G01N 33/74 | (2006.01) | |
| C07K 7/16 | (2006.01) | |
| G01N 33/68 | (2006.01) | |
| G01N 33/577 | (2006.01) | |

(52) U.S. Cl.
CPC .............. *G01N 33/74* (2013.01); *C07K 7/16* (2013.01); *G01N 33/577* (2013.01); *G01N 33/68* (2013.01); *G01N 2410/04* (2013.01); *G01N 2800/04* (2013.01); *G01N 2800/042* (2013.01)

(58) Field of Classification Search
CPC .............. A61K 38/00; A61K 2039/505; C07K 2317/24; C12N 15/52; G01N 33/573
See application file for complete search history.

(56) References Cited

U.S. PATENT DOCUMENTS 7,807,397 B2 * 10/2010 Bergmann ............. G01N 33/74
422/430
2005/0164238 A1 7/2005 Valkirs et al.

FOREIGN PATENT DOCUMENTS

WO   WO-97 35602   10/1997

OTHER PUBLICATIONS

Baglioni et al. (European Journal of Endocrinology, 2004, vol. 151, pp. 605-611) disclose arginine vasopressin mutations linked to neuronal degeneration and hormone deficiency.*
Morgenthaler et al. (Experimental and Clinical Endocrinology & Diabetes, Abstract, 2007) Copeptin secretion patterns.*
Morgenthaler et al. (Clinical Chemistry, vol. 52, No. 1, 2006, pp. 112-119).*
International Search Report for PCT/EP2009/007923 dated Mar. 24, 2010.
Khan, S. Q. et al., "C-Terminal provasopressin (Copeptin) as a Novel and prognostic marker in acute myocardial Infarction Leicester Acute Myocardiol Infarction Peptide (LAMP) Study," Circulation, Apr. 24, 2007, pp. 2103-2110.
Morgenthaler, N. G. et al., "Assay for the measurement of copeptin, a stable peptide derived from the precursor of vasopressin," Clinical Chemistry, 2006, vol. 52, No. 1, pp. 112-119.
Morgenthaler, N. G. et al., "Copeptin: clinical use of a new biomarker," Trends in Endocrinology and Metabolism, Mar. 3, 2008, vol. 19, No. 2, pp. 43-49.
Yi, S. S. et al., "Enhanced expressions of arginine vasopression (Avp) in the hypothalamic paraventricul;ar and supraoptic Nuclei of Type 2 Diabetic Rats," Neurochem Res., 2008, vol. 33, pp. 833-841.
Baglioni et al., European Journal of Endocrinology, 2004, vol. 151, pp. 605-611.
Morgenthaler et al., Experimental and Clinical Endocrinology & Diabetes, Abstract, 2007.

* cited by examiner

*Primary Examiner* — Lisa Cook
(74) *Attorney, Agent, or Firm* — Millen, White, Zelano & Branigan, P.C.

(57) ABSTRACT

Subject of the present invention are assays and in vitro methods for the prediction of the risk of a subject for contracting metabolic syndrome and/or diabetes mellitus and for diagnosing metabolic syndrome, comprising determining the level of arginine vasopressin pro-hormone or fragments thereof in a sample of a subject.

7 Claims, 10 Drawing Sheets

Fig. 1

SEQ ID NO:1 (amino acid sequence of pre-pro-AVP):

```
1    MPDTMLPACF LGLLAFSSAC YFQNCPRGGK RAMSDLELRQ CLPCGPGGKG
51   RCFGPSICCA DELGCFVGTA EALRCQEENY LPSPCQSGQK ACGSGGRCAA
101  FGVCCNDESC VTEPECREGF HRRARASDRS NATQLDGPAG ALLLRLVQLA
151  GAPEPFEPAQ PDAY
```

Fig. 2

SEQ ID NO:2 (amino acid sequence of CT-pro-AVP (copeptin)):

```
1    ASDRSNATQL DGPAGALLLR LVQLAGAPEP FEPAQPDAY
```

Fig. 3

SEQ ID NO:3 (amino acid sequence of pro-AVP):

```
1    CYFQNCPRGG KRAMSDLELR QCLPCGPGGK GRCFGPSICC ADELGCFVGT
51   AEALRCQEEN YLPSPCQSGQ KACGSGGRCA AFGVCCNDES CVTEPECREG
101  FHRRARASDR SNATQLDGPA GALLLRLVQL AGAPEPFEPA QPDAY
```

ARGININE VASOPRESSIN PRO-HORMONE AS PREDICTIVE BIOMARKER FOR DIABETES

FIELD OF THE INVENTION

The present invention is in the field of prognostic biomarkers and prognostic assays. The application particularly relates to the prediction of diabetes and diagnosis of metabolic syndrome.

BACKGROUND OF THE INVENTION

Arginine Vasopressin (AVP), also known as antidiuretic hormone (ADH), is produced in the hypothalamus and released from the neuropituitary gland in conditions of high plasma osmolality, low plasma volume and low blood pressure. AVP binds to three different receptors (V1aR, V1bR and V2R). The V1aR is widely expressed (Nature 1993:356: 523-526), whereas V1bR and V2R are more specifically expressed in the pituitary gland and kidney collecting ducts, respectively (Nature 1992:336-339 and FEBS Lett 1994: 356:215-220). The antidiuretic effect of AVP is mediated through V2R and pharmacological blockade of V2R has favourable effects in the treatment of hyponatremia and heart failure whereas the prothrombotic and vasoconstrictor effects of AVP, which are used clinically in bleeding and hypotensive disorders are primarily mediated through the V1aR. In addition, AVP action has suggested to be linked to modulation of adrenocorticotropic hormone (ACTH) release (V1bR), stimulation of liver glycogenolysis (V1aR) and stimulation of insulin and glucagon secretion (V1aR) (Morel et al., Nature 1992; 356(6369):523-6; de Keyzer et al., FEBS letters 1994; 356(2-3):215-20; Ventura et al., Journal of molecular endocrinology 1999; 22(3):251-60).

Previous studies on humans and animal models have indicated a role of the AVP system in glucose homeostasis, insulin resistance and diabetes mellitus. In patients with poorly controlled diabetes mellitus and increased osmolality, plasma AVP is markedly elevated (Lolait et al., Nature 1992; 357(6376):336-9) and in healthy subjects AVP infusion leads to increased blood glucose levels (Schrier et al., N Engl J Med 2006; 355(20):2099-112). Mice lacking the V1aR display impaired glucose tolerance, insulin resistance and elevated AVP levels (Gheorghiade et al., Jama 2007; 297(12):1332-43; Federici et al., Annals of medicine 2007; 39(5):346-58) while mice who lack the V1bR has the opposite phenotype of lower fasting plasma glucose and increased in insulin sensitivity, in comparison with normal mice (Dunser et al., Circulation 2003; 107(18):2313-9).

The vasopressin gene encodes a precursor protein (pre-pro-AVP) comprising a 19 amino acid signal sequence, arginine vasopressin and two associated proteins, neurophysin II and a glycopeptide, copeptin. Copeptin is a biologically inactive cleavage product of the C-terminus of the AVP precursor and is produced in equimolar amounts with AVP. However, in contrast to AVP, copeptin is stable, has a long half-life, is not bound to platelets and therefore found in considerably higher concentrations in plasma than AVP, and it has been proposed as an alternative diagnostic target to assess vasopressin release (Struck J, Morgenthaler N G, Bergmann A. Copeptin, a stable peptide derived from the vasopressin precursor, is elevated in serum of sepsis patients. Peptides. 2005 December; 26(12):2500-4.).

AVP has been described as diagnostic marker for diabetes mellitus and it was known that AVP level is related with diabetes mellitus as an acute or chronic stressor using type I diabetes mellitus animal models. (Sun Shin Yi et al., Enhanced expressions of arginine vasopressin (Avp) in the hypothalamic paraventricular and supraoptic nucleic of type 2 diabetic rats, Neurochem Res (2008) 33:833-841)

SUMMARY OF THE INVENTION

It was surprisingly found by the present inventors that there is a relation between relatively increased levels of Arginine Vasopressin (AVP) pro-hormone or fragments thereof and the presence of metabolic syndrome and the risk of developing diabetes. In this context a sensitive and precise Copeptin assay comprising at least one monoclonal antibody is provided by the present invention.

A subject of the present invention is thus an in vitro method for predicting the risk of a subject for contracting diabetes mellitus and/or metabolic syndrome or for identifying a subject having an enhanced risk for contracting diabetes mellitus and/or metabolic syndrome or for diagnosing metabolic syndrome in a subject, comprising the following steps:

a. providing a sample from said subject,
   b. determining the level of arginine vasopres sin pro-hormone or fragments thereof in said sample,
   c. using said level of arginine vasopressin pro-hormone or fragments thereof for the prediction of the probability of the subject to contract diabetes mellitus and/or metabolic syndrome or for inferring from it a risk for contracting diabetes mellitus and/or metabolic syndrome for said subject or for diagnosing metabolic syndrome in said subject.

A further subject of the present invention is a sensitive and precise copeptin assay.

BRIEF DESCRIPTION OF DRAWINGS

FIG. 1: Amino acid sequence of pre-pro-AVP (SEQ ID NO:1).

FIG. 2: Amino acid sequence of CT-pro-AVP (copeptin) (SEQ ID NO:2).

FIG. 3: Amino acid sequence of pro-AVP (SEQ ID NO:3).

DETAILED DESCRIPTION OF THE INVENTION

Figure 4:
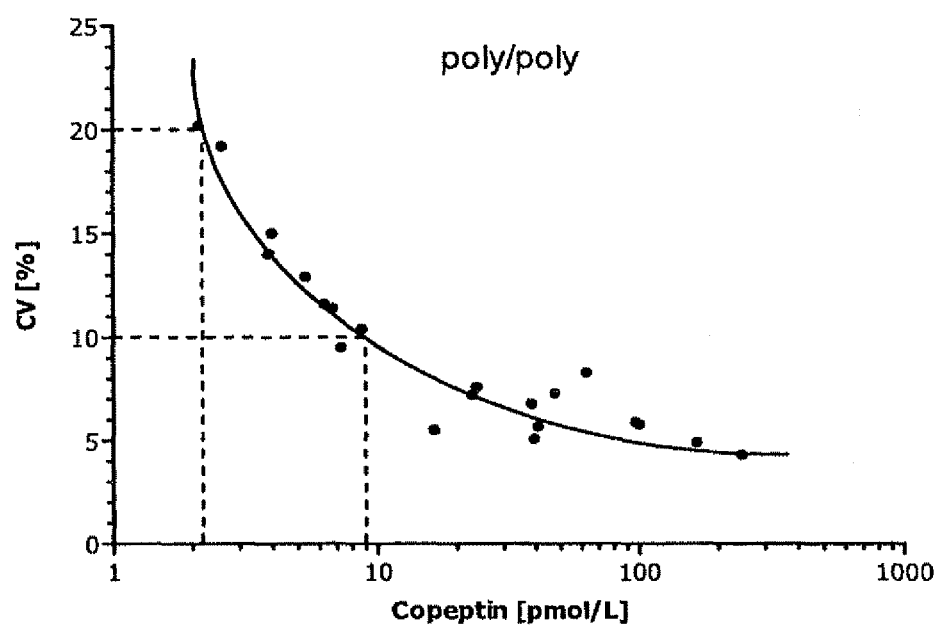
FIG. 4: Precision profile for the polyclonal/polyclonal antibody copeptin assay. Inter-assay Coefficient of Variation (CV [%]) plotted against copeptin concentrations [pmol/L]. Copeptin concentrations, which are determined with a CV of 10% and 20%, respectively, are indicated.

The present invention relates to a method for predicting the risk of a subject for contracting diabetes mellitus and/or metabolic syndrome or for identifying a subject having an enhanced risk for contracting diabetes mellitus and/or metabolic syndrome or for diagnosing metabolic syndrome in a subject, comprising the following steps:
  a. providing a sample from said subject,
  b. determining the level of arginine vasopres sin pro-hormone or fragments thereof in said sample,
  c. using said level of arginine vasopressin pro-hormone or fragments thereof for the prediction of the probability of the subject to contract diabetes mellitus and/or metabolic syndrome or for inferring from it a risk for contracting diabetes mellitus and/or metabolic syndrome for said subject or for diagnosing metabolic syndrome in said subject.

Herein, "using said level of arginine vasopressin pro-hormone or fragments thereof for the prediction of the probability of the subject to contract diabetes mellitus and/or metabolic syndrome or for inferring from it a risk for contracting diabetes mellitus and/or metabolic syndrome for said subject or for diagnosing metabolic syndrome in said subject" may have the meaning of "correlating said level of arginine vasopressin pro-hormone or fragments thereof with the risk of the subject to contract diabetes mellitus and/or metabolic syndrome or with the diagnosis of metabolic syndrome in said subject".

In a preferred embodiment for all aspects of the invention said subject is apparently healthy.

"Apparently healthy", as used herein, relates to individuals who do not suffer from diabetes mellitus. In some embodiments, the apparently healthy subjects are suffering from metabolic syndrome. The inventive method may be used for diagnosing whether a subject has metabolic syndrome or not.

The term "subject" as used herein refers to a living human or non-human organism. Preferably herein the subject is a human subject.

Preferably, said subject is non-diabetic.

In a very particular embodiment the apparently healthy subjects are individuals who have not previously had or are not aware of having had a cardiovascular or a coronary event or heart failure or are not suffering from a cardiovascular disease. Coronary events are defined as fatal or non-fatal acute coronary syndromes including myocardial infarction, or death due to ischemic heart disease. Cardiovascular events are defined as fatal or non-fatal acute coronary syndromes including myocardial infarction, fatal or non-fatal stroke, or death due to cardiovascular disease. Additionally, the apparently healthy subjects may in a very particular embodiment not have an acute infectious disease.

In another very particular embodiment, the apparently healthy subjects may be suffering from a cardiovascular disease and/or may have had a cardiovascular or a coronary event or heart failure. In certain embodiments they may be suffering from an infectious disease.

In one embodiment the subject exhibits impaired fasting glycaemia (impaired fasting glucose), i.e. a fasting glucose level in the blood (fasting blood glucose (FBG) or fasting blood sugar (FBS)) of less than 6.1 but more than 5.4 mmol/L. Thus, in an especially preferred embodiment said subject is a non-diabetic with fasting blood glucose of less than 6.1 mmol/L but more than 5.4 mmol/L.

In another especially preferred embodiment said subject is a subject without impaired fasting glycaemia. Thus, in a especially preferred embodiment said subject is a subject with fasting blood glucose of less than 5.4 mmol/L.

Fasting blood glucose is measured at least 8 hours after the last food intake of the subject, typically 8 to 10 hours after the last food intake.

(Fasting) blood glucose levels herein are given in terms of whole blood glucose levels. In general, glucose can be measured in whole blood, serum or plasma, but reference values differ depending on the type of sample.

Determining (or measuring or detecting) the level of arginine vasopressin pro-hormone or fragments thereof herein is performed using a diagnostic assay as explained below.

A preferred fragment of arginine vasopres sin pro-hormone (pro-AVP) is C-terminal pro-AVP (CT-pro-AVP or Copeptin), i.e. a posttranslationally modified (glycosylated) peptide covering amino acid positions 107-145 of pro-AVP (126-164 of pre-pro-AVP).

In a preferred embodiment the fragment of arginine vasopressin pro-hormone (pro-AVP) is not the mature AVP.

In a particularly preferred embodiment of the method, the level of copeptin is determined.

As mentioned herein in the context of pro-hormones and other peptides, the term "fragment" refers to smaller proteins or peptides derivable from larger proteins or peptides, which hence comprise a partial sequence of the larger protein or peptide. Said fragments are derivable from the larger proteins or peptides by saponification of one or more of its peptide bonds.

"Fragments" of arginine vasopressin pro-hormone (pro-AVP) preferably relate to fragments of at least 6 amino acids in length, most preferably at least 12 amino acid residues in length. Such fragments are preferably detectable with immunological assays as described herein.

In the context of the present invention, the term "level" in expressions such as "level of a pro-hormone" and similar expressions, refers to the quantity of the molecular entity mentioned in the respective context, or in the case of enzymes it can also refer to the enzyme activity.

The methods according to the present invention are especially well suited for the prediction of the risk of developing diabetes type II.

The prediction of the risk of the subject for contracting diabetes mellitus and/or metabolic syndrome or the diagnosis of metabolic syndrome may in one embodiment be improved by additionally determining and using the level of at least one laboratory parameter or further marker selected from the group comprising fasting blood or plasma glucose, triglycerides, high-density lipoprotein (HDL) cholesterol or subfractions thereof, low-density lipoprotein (LDL) cholesterol or subfractions thereof, Cystatin C, Insulin, C-reactive protein (CRP), natriuretic peptides of the A- and the B-type as well as their precursors and fragments thereof including type A natriuretic peptide (ANP), proANP, N-terminal-proANP (NT-proANP), midregional-proANP (MR-proANP), type B natriuretic peptide (BNP), proBNP, N-terminal-proBNP (NT-proBNP), growth differentiation factor 15 (GDF15), interleukin 1 receptor-like 1 (ST2), procalcitonin and fragments thereof, pro-Adrenomedullin and fragments thereof including adreneomedullin (ADM), Proadrenomedullin N-terminal 20 peptide (PAMP), mid-regional-proADM (MR-proADM), C-terminal proADM (CT-proADM) pro-Endothelin-1 and fragments thereof including C-terminal-proET-1 (CT-proET-1), N-terminal-proET-1 (NT-proET-1), big-Endothelin-1 and Endothelin-1.

In particular embodiments of the invention, additionally at least one clinical parameter is determined selected from the group comprising age, gender, systolic blood pressure, diastolic blood pressure, antihypertensive treatment (AHT), body mass index, waist circumference, waist-hip-ratio, current smoker, diabetes heredity and previous cardiovascular disease (CVD).

According to the World Health Organization (WHO), diabetes is a chronic disease, which occurs when the pancreas does not produce enough insulin, or when the body cannot effectively use the insulin it produces. This leads to an increased concentration of glucose in the blood (hyperglycaemia). Type 1 diabetes (previously known as insulin-dependent or childhood-onset diabetes) is characterized by a lack of insulin production. Type 2 diabetes (formerly called non-insulin-dependent or adult-onset diabetes) is caused by the body's ineffective use of insulin. It often results from excess body weight and physical inactivity.

Diabetes mellitus type 2 or Type 2 diabetes is a metabolic disorder that is primarily characterized by insulin resistance, relative insulin deficiency, and hyperglycaemia. The World Health Organization definition of diabetes is for a single raised glucose reading with symptoms, otherwise raised values on two occasions, of either: (i) fasting plasma glucose ≥7.0 mmol/l (126 mg/dl) or (ii) with a Glucose tolerance test (GTT), two hours after the oral dose a plasma glucose ≥11.1 mmol/l (200 mg/dl). A common initial symptom of type 2 diabetes is a faint smell of fruit or vegetable odour on the breath. This is caused by ketosis induced by lack of response to insulin, leading to lack of glucose internal to cells. It commonly accompanies high blood glucose levels, which are also a result of decreased sensitivity to insulin.

Metabolic syndrome is a combination of medical disorders that increase the risk of developing cardiovascular disease and diabetes. It affects a great number of people, and prevalence increases with age. Some studies estimate the prevalence in the USA to be up to 25% of the population. Metabolic syndrome is also known as metabolic syndrome X, syndrome X, insulin resistance syndrome, Reaven's syndrome, and CHAOS (Australia). It is important to identify those individuals with metabolic syndrome early, so that lifestyle interventions and treatment may prevent the development of diabetes and/or cardiovascular disease. The underlying cause of the metabolic syndrome continues to challenge the experts. Both insulin resistance and central obesity are considered significant factors. Genetics, physical inactivity, ageing, a proinflammatory state and hormonal changes may also have a causal effect, but the role of these may vary depending on ethnic group. As a consequence of the uncertainty about the mechanistic cause of the metabolic syndrome a lot of confusion has existed about the definition of the metabolic syndrome. The existence of multiple definitions for the metabolic syndrome has caused confusion and has resulted in many studies and research papers comparing the merits of each definition. According to the Executive Summary of The Third Report of The National Cholesterol Education Program (NCEP) Expert Panel on Detection, Evaluation, And Treatment of High Blood Cholesterol In Adults (Adult Treatment Panel III) (JAMA. 2001; 285(19):2486-2497) metabolic syndrome is defined as the presence of three or more of the following components as follows: (1) Waist circumference.gtoreq.88 cm (35 inches) in women or .gtoreq.102 cm (40 inches) in men, (2) BP.gtoreq.130/85 mmHg or treatment for hypertension, (3) fasting triglycerides.gtoreq.150 mg/dL, (4) HDL cholesterol.ltoreq.40 mg/dL in men or .ltoreq.50 mg/dL in women, and (5) fasting blood glucose.gtoreq.110 mg/dL or treatment for diabetes. A more recent definition with some modifications has been given by the International Diabetes Federation; see, e.g., *The IDF Consensus Worldwide Definition of the Metabolic Syndrome*, published by IDF 2006. As the goal of defining the metabolic syndrome is the identification of subjects at increased risk for developing diabetes and/or cardiovascular diseases, prognostic factors independently associated with such risk can be directly associated with the metabolic syndrome and in that sense are diagnostic for the presence of the metabolic syndrome. Accordingly, a marker, which is independently predictive for the development of diabetes, as is shown for copeptin in the present invention, has to be considered at the same time a diagnostic marker (along with other diagnostic laboratory and clinical parameters) for the presence of the metabolic syndrome, and it can even be anticipated that it will become part of the definition of the metabolic syndrome in the future.

Thus, the determined levels of arginine vasopressin pro-hormone or fragments thereof in a sample of subjects may be used in conjunction with other clinical and/or laboratory parameters to help to define "metabolic syndrome" as a medical condition. In other words, the level of arginine vasopressin pro-hormone or fragments thereof may be used as additional parameter to improve the definition of metabolic syndrome in terms of decisive criteria since the current criteria as outlined above do not in all cases lead to satisfactory results.

Insulin resistance (IR) is a state in which a given concentration of insulin produces a less-than-expected biological effect. Insulin resistance has also been arbitrarily defined as the requirement of 200 or more units of insulin per day to attain glycemic control and to prevent ketosis. High plasma levels of insulin and glucose due to insulin resistance often lead to metabolic syndrome and type 2 diabetes, including its complications. Symptoms of IR may comprise fatigue, brain fogginess, inability to focus, low blood sugar, intestinal bloating, sleepiness, weight gain, fat storage, difficulty losing weight, increased blood triglyceride levels, increased blood pressure, and depression.

The invention also pertains to a method for predicting the risk of a subject for contracting diabetes mellitus and/or metabolic syndrome or for identifying a subject having an enhanced risk for contracting diabetes mellitus and/or metabolic syndrome or for diagnosing metabolic syndrome in a subject as described above, wherein the level of arginine vasopressin pro-hormone or fragments thereof either alone or in conjunction with other prognostically useful laboratory or clinical parameters is used for the prediction of the risk of a subject for contracting diabetes mellitus and/or metabolic syndrome or for the diagnosis of metabolic syndrome by a method which may be selected from the following alternatives:

Comparison with the median of the level of arginine vasopressin pro-hormone or fragments thereof in an ensemble of pre-determined samples in a population of apparently healthy subjects, Comparison with a quantile of the level of arginine vasopressin pro-hormone or fragments thereof in an ensemble of pre-determined samples in a population of apparently healthy subjects, Calculation based on Cox Proportional Hazards analysis or by using Risk index calculations such as the NRI (Net Reclassification Index) or the IDI (Integrated Discrimination Index).

In a preferred embodiment the level of arginine vasopressin (AVP) pro-hormone or fragments thereof having at least a length of 12 amino acids is determined in a diagnostic assay, preferably by an immunoassay. It is particularly preferred that the level of copeptin or fragments thereof having at least a length of 12 amino acids is determined.

The invention may also involve comparing the level of a marker (here arginine vasopressin pro-hormone or fragments thereof such as copeptin) for the individual with a predetermined value. The predetermined value can take a variety of forms. It can be single cut-off value, such as for instance a median or mean or the 75th, 90th, 95th or 99th percentile of a population. It can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quartiles, the lowest quartile being individuals with the lowest risk and the highest quartile being individuals with the highest risk.

The predetermined value can vary among particular populations selected, depending on their habits, ethnicity, genetics etc. For example, an apparently healthy, non-smoker population (no detectable disease, particularly no diabetes mellitus) might have a different 'normal' range of markers than a smoking population or a population the members of which have diabetes mellitus. Accordingly, the predetermined values selected may take into account the category in which an individual falls. Appropriate ranges and categories can be selected with no more than routine experimentation by those of ordinary skill in the art.

In a specific embodiment of the method according to the invention the use of said level of arginine vasopressin pro-hormone or fragments thereof comprises comparing said level of arginine vasopressin pro-hormone or fragments thereof to a threshold level, whereby, when said level of arginine vasopressin pro-hormone or fragments thereof exceeds said threshold level, diabetes mellitus and/or metabolic syndrome is predicted in a subject or a subject having an enhanced risk for getting diabetes mellitus and/or metabolic syndrome is identified.

Other preferred cut-off values are for instance the 90th, 95th or 99th percentile of a normal population. By using a higher percentile than the 75th percentile, one reduces the number of false positive subjects identified, but one might miss to identify subjects, who are at moderate, albeit still increased risk. Thus, one might adopt the cut-off value depending on whether it is considered more appropriate to identify most of the subjects at risk at the expense of also identifying "false positives", or whether it is considered more appropriate to identify mainly the subjects at high risk at the expense of missing several subjects at moderate risk.

Other mathematical possibilities to calculate an individual's risk by using the individual's copeptin value and other prognostic laboratory and clinical parameters are for instance based on Cox regression analysis or are the NRI (Net Reclassification Index) or the IDI (Integrated Discrimination Index). The indices can be calculated according to Pencina (Pencina M J, et al.: Evaluating the added predictive ability of a new marker: from area under the ROC curve to reclassification and beyond. Stat Med. 2008; 27:157-172).

For instance a copeptin level of 5.04 pmol/L (i.e. the median concentration of a reference population of apparently healthy subjects) or above, preferably above 7.93 pmol/L (i.e. the Q3/Q4 border concentration of a reference population of apparently healthy subjects) in the sample may be indicative for an elevated risk of the patient to contract diabetes mellitus. Q1, Q2, Q3 and Q4 herein refer to quartiles of a reference population of apparently healthy subjects.

In a further particular aspect the invention pertains to a method for diagnosing metabolic syndrome in a subject comprising the following steps:
 a. providing a sample from said subject,
 b. determining the level of arginine vasopres sin pro-hormone or fragments thereof in said sample
 c. determining other clinical and/or laboratory parameters associated with the diagnosis of metabolic syndrome
 d. correlating the level of arginine vasopres sin pro-hormone or fragments thereof in conjunction with other clinical and/or laboratory parameters associated with the diagnosis of metabolic syndrome.

Also within the scope of the present invention is an assay for the determination of the copeptin level in a sample for predicting the risk of a subject to contract diabetes mellitus and/or metabolic syndrome or diagnosing metabolic syndrome.

Preferably, the assay has a total assay imprecision of 20% coefficient of variation (CV) at a concentration below 2.2 pmol/L and a lower than 20% CV at normal range-concentrations above that concentration, and/or 10% CV at a concentration below 9 pmol/l and a lower than 10% CV at normal range-concentrations above that concentration.

In another preferred embodiment, the total assay imprecision of maximally 12% at the median Copeptin concentration determined in serum or plasma of a Caucasian population of healthy fasting females at rest.

In a preferred embodiment of the above described assays, the assay comprises two anti-copeptin antibodies, wherein at least one of the antibodies is a monoclonal antibody or fragment or recombinant variant thereof The invention also relates to an assay for the determination of the copeptin level in a sample, wherein the assay comprises two anti-copeptin antibodies, wherein at least one of the antibodies is a monoclonal antibody or fragment or recombinant variant thereof.

Preferably, the assay comprises a monoclonal and a polyclonal antibody.

In another preferred embodiment of the assays of the invention, one monoclonal antibody binds an epitope comprised in a peptide representing positions 132-147 of pre-pro-vasopressin.

The levels of the markers as obtained by the methods or by the use of the assays according to the present invention may be analyzed in a number of fashions well known to a person skilled in the art. For example, each assay result obtained may be compared to a "normal" value, or a value indicating a particular disease or outcome. A particular diagnosis/prognosis may depend upon the comparison of each assay result to such a value, which may be referred to as a diagnostic or prognostic "threshold". In certain embodiments, assays for one or more diagnostic or prognostic indicators are correlated to a condition or disease by merely the presence or absence of the indicator(s) in the assay. For example, an assay can be designed so that a positive signal only occurs above a particular threshold concentration of interest, and below which concentration the assay provides no signal above background.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy) and "disease" populations (i.e. patients suffering from diabetes, insulin resistance and/or metabolic syndrome). For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art. See, e.g., Hanley et al., *Radiology* 143: 29-36 (1982). Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In certain embodiments, particular thresholds for one or more markers in a panel are not relied upon to determine if a profile of marker levels obtained from a subject are indicative of a particular diagnosis/prognosis. Rather, the present invention may utilize an evaluation of a marker panel "profile" as a unitary whole. A particular "fingerprint" pattern of changes in such a panel of markers may, in effect, act as a specific diagnostic or prognostic indicator. As discussed herein, that pattern of changes may be obtained from a single sample, or from temporal changes in one or more members of the panel (or a panel response value). A panel herein refers to a set of markers.

As described hereinafter, a panel response value is preferably determined by plotting ROC curves for the sensitivity of a particular panel of markers versus 1-(specificity) for the panel at various cut-offs. In these methods, a profile of marker measurements from a subject is considered together to provide a global probability (expressed either as a numeric score or as a percentage risk) of a diagnosis or prognosis. In such embodiments, an increase in a certain subset of markers may be sufficient to indicate a particular diagnosis/prognosis in one patient, while an increase in a different subset of markers may be sufficient to indicate the same or a different diagnosis/prognosis in another patient. Weighting factors may also be applied to one or more markers in a panel, for example, when a marker is of particularly high utility in identifying a particular diagnosis/prognosis, it may be weighted so that at a given level it alone is sufficient to signal a positive result. Likewise, a weighting factor may provide that no given level of a particular marker is sufficient to signal a positive result, but only signals a result when another marker also contributes to the analysis.

In certain embodiments, markers and/or marker panels are selected to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group. In certain preferred embodiments, markers and/or marker panels are preferably selected to exhibit a positive or negative likelihood ratio of at least about 1.5 or more or about 0.67 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain preferred embodiments, markers and/or marker panels are preferably selected to exhibit an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain preferred embodiments, markers and/or marker panels are preferably selected to exhibit a hazard ratio of at least about 1.1 or more or about 0.91 or less, more preferably at least about 1.25 or more or about 0.8 or less, still more preferably at least about 1.5 or more or about 0.67 or less, even more preferably at least about 2 or more or about 0.5 or less, and most preferably at least about 2.5 or more or about 0.4 or less. The term "about" in this context refers to +/−5% of a given measurement.

The skilled artisan will understand that associating a diagnostic or prognostic indicator, with a diagnosis or with a prognostic risk of a future clinical outcome is a statistical analysis. For example, a marker level of greater than X may signal that a patient is more likely to suffer from an adverse outcome than patients with a level less than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In yet other embodiments, multiple determinations of diagnostic or prognostic markers can be made, and a temporal change in the marker can be used to determine a diagnosis or prognosis. For example, a marker concentration in a subject sample may be determined at an initial time, and again at a second time from a second subject sample. In such embodiments, an increase in the marker from the initial time to the second time may be indicative of a particular diagnosis, or a particular prognosis. Likewise, a decrease in the marker from the initial time to the second time may be indicative of a particular diagnosis, or a particular prognosis.

The term "sample" as used herein refers to a sample of bodily fluid obtained for the purpose of diagnosis, prognosis, or evaluation of a subject of interest, such as a patient. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, in a preferred embodiment of the invention the sample is selected from the group comprising a blood sample, a serum sample, a plasma sample, a cerebrospinal fluid sample, a saliva sample and a urine sample or an extract of any of the aforementioned samples. Preferably, the sample is a blood sample, most preferably a serum sample or a plasma sample.

The term "correlating," as used herein in reference to the use of diagnostic and prognostic markers, refers to comparing the presence or amount of the marker(s) in a patient to its presence or amount in persons known to suffer from, or known to be at risk of, a given condition; or in persons known to be free of a given condition. As discussed above, a marker level in a patient sample can be compared to a level known to be associated with a specific diagnosis. The sample's marker level is said to have been correlated with a diagnosis; that is, the skilled artisan can use the marker level to determine whether the patient suffers from a specific type diagnosis, and respond accordingly. Alternatively, the sample's marker level can be compared to a marker level known to be associated with a good outcome (e.g., the absence of disease, etc.). In preferred embodiments, a profile of marker levels is correlated to a global probability or a particular outcome.

The invention also pertains to a method for the stratification of a patient into risk groups, said method comprising the steps as described above.

The present invention also pertains to the use of any of the above described assays for predicting the risk of a subject for developing diabetes mellitus type II.

The invention further relates to the use of an immunoassay for a method according to the invention, wherein at least one anti-copeptin antibody or fragment or recombinant variant thereof is used to determine the level of copeptin or molecular variants thereof in a sample. Preferably, the at least one anti-copeptin antibody is a monoclonal antibody.

Preferably, the immunoassay is a sandwich assay and wherein additionally to the first anti-copeptin antibody a second anti-copeptin antibody is used to determine the level of copeptin or molecular variants thereof in a sample. Preferably, at least one of said antibodies is a monoclonal antibody.

Also within the scope of the present invention is the in vitro use of a capture probe directed against vasopres sin or fragments thereof or its precursors or fragments thereof for predicting the risk of an apparently healthy subject for contracting diabetes mellitus and/or metabolic syndrome or for diagnosing metabolic syndrome in a subject. Preferably, the capture probes are directed against one ore more epitopes located in amino acid positions 126-164 of pre-pro-AVP.

The invention also relates to a monoclonal antibody or fragment or recombinant variant thereof which binds an epitope comprised in a peptide representing positions 132-147 of pre-pro-AVP.

Fragments or recombinant variants of said monoclonal antibody exhibit at least 80% of the affinity of said monoclonal antibody to pre-pro-AVP. Preferably, fragments or recombinant variants of said monoclonal antibody exhibit at least 80% of the affinity of said monoclonal antibody to the epitope comprised in a peptide representing positions 132-147 of pre-pro-AVP. This is a preferred prerequisite for the present invention as only the before-mentioned fragments and recombinant variant are as useful as the monoclonal antibody for providing an assay according to the present invention which is an assay that has a total assay imprecision of 20% CV at a concentration below 2.2 pmol/L and a lower than 20% CV at normal range-concentrations above that concentration, and/or 10% CV at a concentration below 9 pmol/l and a lower than 10% CV at normal range-concentrations above that concentration. This assay may be provided if at least one of the antibodies is a monoclonal antibody or a fragment or recombinant variant thereof that exhibits at least 80% of the affinity of said monoclonal antibody to the epitope comprised in a peptide representing positions 132-147 of pre-pro-AVP.

The invention also relates to the use of a capture probe directed against arginine vasopressin pro-hormone or fragments thereof for predicting the risk of a subject for contracting diabetes mellitus and/or metabolic syndrome or for diagnosing metabolic syndrome. Preferably, the capture probes are directed against one ore more epitopes located in amino acid positions 126-164 of pre-pro-vasopres sin (pre-pro-AVP).

In a further aspect, the present invention relates to the use of any of the above described assays or methods in a prophylactic therapy against diabetes mellitus, insulin resistance and/or metabolic syndrome.

The amino acid sequence of pre-pro-AVP is given in SEQ ID NO:1 (FIG. 1). The amino acid sequence of copeptin is given in SEQ ID NO:2 (FIG. 2). Copeptin may be glycosylated. Pre-pro-AVP is the precursor peptide for arginine vasopressin pro-hormone (pro-AVP, SEQ ID NO:3, FIG. 3) and its fragments (including arginine vasopressin, neurophysin II and copeptin). In addition to pro-AVP pre-pro-AVP comprises an N-terminal 19 amino acid signal sequence. Unless otherwise stated all sequence specifications herein refer to the sequence of pre-pro-AVP.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ $M^{-1}$.

In the context of the present invention, "capture molecules" are molecules which may be used to bind target molecules or molecules of interest, i.e. analytes (i.e. in the context of the present invention the cardiovascular peptide(s)), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a RNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

The preferred detection methods comprise immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

The assays can be homogenous or heterogeneous assays, competitive and non-competitive sandwich assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (The Immunoassay Handbook, Ed. David Wild, Elsevier LTD, Oxford; 3rd ed. (May 2005), ISBN-13: 978-0080445267; Hultschig C et al., Curr Opin Chem Biol. 2006 February; 10(1):4-10. PMID: 16376134, incorporated herein by reference).

In a particularly preferred embodiment the assay comprises two capture molecules, preferably antibodies which are both present as dispersions in a liquid reaction mixture, wherein a first labelling component is attached to the first capture molecule, wherein said first labelling component is part of a labelling system based on fluorescence- or chemiluminescence-quenching or amplification, and a second labelling component of said marking system is attached to the second capture molecule, so that upon binding of both capture molecules to the analyte a measurable signal is generated that allows for the detection of the formed sandwich complexes in the solution comprising the sample.

Even more preferred, said labelling system comprises rare earth cryptates or rare earth chelates in combination with a fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), RHODAMINE, RHODAMINE GREEN, RHODAMINE RED, RHODAMINE 110, BODIPY dyes, such as BODIPY TMR, OREGON GREEN, Coumarines such as Umbelliferone, Benzimides, such as Hoechst 33258; Phenanthridines, such as TEXAS RED, YAKIMA YELLOW, ALEXA FLUOR, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, Encyclopedia of chemical technology, $4^{th}$ ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridinium esters.

Figure 5:
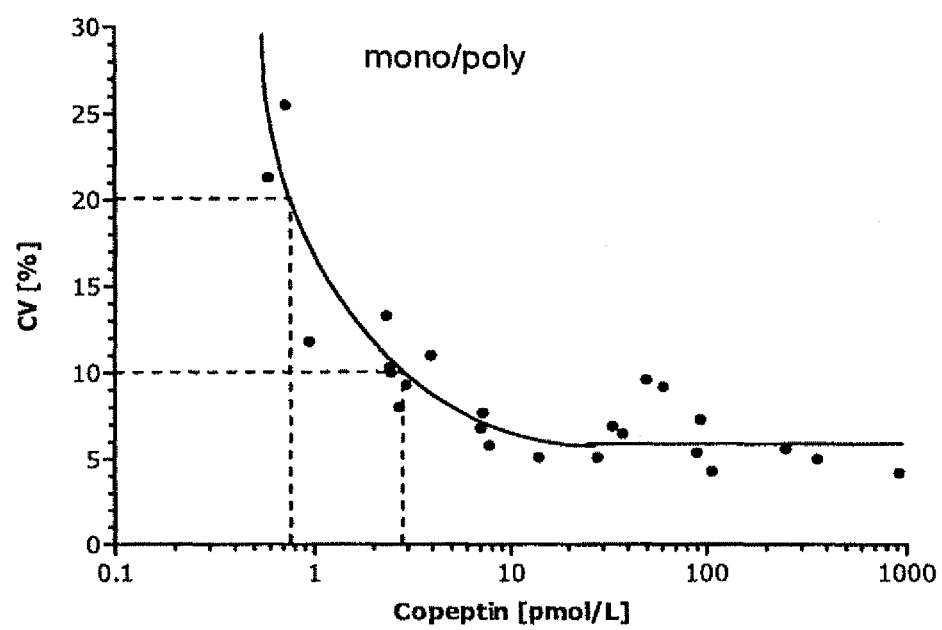
FIG. 5: Precision profile for the monoclonal/polyclonal antibody copeptin assay. Inter-assay CV [%] plotted against copeptin concentrations [pmol/L]. Copeptin concentrations, which are determined with a CV of 10% and 20%, respectively, are indicated.

The most preferred embodiment wherein the assay comprises a monoclonal and a polyclonal antibody was compared to an assay comprising two polyclonal antibodies. To comparatively assess the precision of both assays, the total assay imprecision was determined by measuring, in duplicate, 22 human serum samples with various copeptin concentrations. These data were generated by 6 different operators in 12 assay runs, with 2 different lots of reagents in 2 different laboratories. The resulting precision profiles are shown in FIGS. 4 and 5. For the poly/poly assay, the 20% CV was obtained at 2.2 pmol/L and 10% CV at 9 pmol/L. In contrast, for the mono/poly assay, the 20% CV was obtained at 0.75 pmol/L and 10% CV at 2.9 pmol/L.

The median copeptin concentrations of healthy fasting females at rest has been reported to be 3.2 pmol/L (Bhandari S S, Loke I, Davies J E, Squire I B, Struck J, Ng L L. Gender and renal function influence plasma levels of copeptin in healthy individuals. Clin Sci (Lond). 2008 Jul. 22. [Epub ahead of print]) and 3.7 pmol/L (Morgenthaler N G, Struck J, Alonso C, Bergmann A. Assay for the measurement of copeptin, a stable peptide derived from the precursor of vasopressin. Clin Chem. 2006 January; 52(1):112-9.). In the present analysis the total assay imprecision at 3.2 pmol/L was determined to be 15% for the poly/poly assay, whereas it was 9.5% for the mono/poly assay. Thus, clearly the mono/poly assay is much more suitable to assess copeptin levels in the normal population. Both assays are described in detail below:

Assay 1 (Poly/Poly)

Determination of Copeptin in the chemiluminescence/coated-tube format was performed as described (Morgenthaler N G, Struck J, Alonso C, Bergmann A. Assay for the measurement of copeptin, a stable peptide derived from the precursor of vasopressin. Clin Chem. 2006 January; 52(1): 112-9.). Briefly, the tubes were coated with a purified sheep polyclonal antibody (2 µg/tube) raised against a peptide representing positions 132-147 of pre-pro-Vasopressin. A purified sheep polyclonal antibody raised against a peptide representing positions 149-164 of pre-pro-Vasopressin was labelled with MACN-Akridinium-N-hydroxysuccinimide-Ester and used as tracer. Dilutions of a peptide representing positions 132-164 of pre-pro-AVP in normal horse serum served as standards. The immunoassay was performed by incubating 50 µl of samples/standards and 200 µl tracer in coated tubes for 2 hours at room temperature. The tubes were washed 4 times with 1 ml of LUMItest wash solution (B.R.A.H.M.S. AG, Hennigsdorf Germany), and bound chemiluminescence was measured with an LB952T luminometer (Berthold, Bad Wildbach Germany).

Assay 2 (Mono/Poly)

A monoclonal antibody (294/1A7) was developed, which has an epitope in Copeptin located in the corresponding positions 132-147 of pre-pro-Vasopressin. The antibody was developed employing standard procedures as described (Harlow E, Lane D "Antibodies—A Laboratory Manual" 1988 by Cold Spring Harbor Laboratory, pages 148 ff, ISBN 0-87969-314-2). Briefly, a chemically synthesized peptide representing positions 132-164 of pre-pro-Vasopressin and extended by an additional cysteine residue at the N-terminus was coupled to BSA by using Sulfo-MBS as crosslinker. Balb/c mice were immunized and boostered with this conjugate. Spleen cells of the immunized mice were fused with a SP2/0 myeloma cell line, and anti-Copeptin producing hybridoma cells were selected by their ability to secrete antibodies recognizing a peptide covering positions 132-147 of pre-pro-Vasopressin. Positively selected hybridoma cells were recloned, leading to several hybridoma cell lines, one them producing monoclonal antibody 294/1A7, which was further used.

The monoclonal antibody was used to replace the polyclonal antibody used on the solid phase in poly/poly assay described above. All other assay components and performance of the assay was unchanged as compared to the poly/poly assay described above.

With the methods and assays of the present invention the risk of a subject to contract diabetes mellitus and/or metabolic syndrome can be determined. In other cases a diagnosis of metabolic syndrome, preferably in combination with other clinical and/or laboratory parameters, in a subject may be performed. From the results of the methods and assays of the present invention, a suitable treatment or prevention strategy may be chosen for a subject. Subjects with increased risk for contracting metabolic syndrome and/or diabetes mellitus are advised to change their lifestyles, e.g. to moderately decrease their daily caloric intake, change the dietary composition and/or increase the physical activities.

The correlation between the level arginine vasopressin pro-hormone or fragments thereof in samples of subjects with their risk to contract diabetes mellitus and/or metabolic syndrome as found by the present inventors, suggests a role of the vasopressin system in glucose homeostasis and diabetes development. Increased levels of vasopressin (and its pro-hormone and fragments thereof) are associated with diabetes mellitus and metabolic syndrome. The effect of vasopressin may particularly be mediated through the V1b receptor (V1bR). Thus, the present invention also pertains to the treatment or prevention of metabolic syndrome and/or diabetes mellitus by inhibiting the V1bR receptor. The present invention relates to V1bR antagonists for the use in the treatment and/or prevention of metabolic syndrome and/or diabetes mellitus. Particularly preferred V1bR antagonists may be selected from the group comprising antibodies and small molecules. Possible V1bR antagonists may be identified in binding assays known to a skilled person by identifying their $IC_{50}$ values, e.g. using a radio receptor assay.

EXAMPLES

Example 1

Clinical Study

The Malmö Diet and Cancer study (MDC) is a population-based prospective cohort consisting of 28,449 persons surveyed in 1991-1996 From this cohort, 6103 persons were randomly selected to be studied for the epidemiology of carotid artery disease, referred to as the MDC cardiovascular cohort (MDC-CC). Fasting plasma samples were obtained in 5405 subjects in the MDC-CC. Of those, complete data on covariates, including known risk factors for diabetes, potential confounders and copeptin in plasma (P-copeptin), was available in 4742 individuals (Table 1).

Diabetes at the baseline exam was defined as self report of a physician diagnosis or use of anti-diabetic medication or fasting blood glucose (FBG) of ≥6.1 mmol/L. All analyses in plasma and blood were performed in over-night fasting samples. FBG was measured in whole blood by a hexokinase-glucose-6-phosphate dehydrogenase method. LDL cholesterol was calculated according to Friedewald's formula. In fasting plasma samples which had been stored at −80° C., we measured copeptin using Assay 2 (mono/poly) as described above. C-reactive protein (CRP) was measured by a high-sensitivity assay (Tina-quant CRP, Roche Diagnostics, Basel, Switzerland). Cystatin C was measured using a particle-enhanced immuno-nephelometric assay (N Latex Cystatin C, Dade Behring, Ill.).

Blood pressure was measured using a mercury-column sphyngomanometer after 10 minutes of rest in the supine position. Cigarette smoking was elicited by a self-administered questionnaire, with current cigarette smoking defined as any smoking within the past year. Previous cardiovascular disease was defined as presence of myocardial infarction or stroke prior to the baseline exam. Diabetes heredity was elicited by a questionnaire and defined as known diabetes in at least one first degree relative.

New onset diabetes after the baseline exam until June 2007 was assessed by three registers: (1) The HbA1c-register of Malmö (MHR) at the Department of Clinical Chemistry, Malmö University Hospital, which analysed and catalogued all HbA1c samples taken in institutional and non-institutional care in the great Malmö area from 1990 and onwards. In the MHR, individuals were defined as having diabetes if they had at least two HbA1c recordings ≥6.0% using the Swedish Mono-S standardization system, which corresponds to 7.0% according to the US National Glycohemoglobin Standardization Program (NGSP) or at least three HbA1c recordings ≥5.5% (corresponding to 6.5% according to NGSP). (2) The Swedish National Diabetes Register (NDR), which was initiated in 1996 and covered approximately 50% of all diabetes patients in Sweden in 2007; (3) A regional register of the Scania Region in which Malmö is the main city (Diabetes 2000 registry) (Lindholm E, Eur J Epidemiol 2001:17:983-989), which was initiated in 2000 and covered approximately 25% of all diabetes patients in the Scania region in 2001.

Subjects who did not appear in any of the three registers before the baseline exam and were free from diabetes at the baseline exam in the MDC-CC according to our criteria (i.e. no self reported history of physician diagnosed diabetes, absence of anti-diabetic therapy, FBG at the baseline exam of <6.0 mmol/L) and were registered as diabetes patients in the NDR or Diabetes 2000 registry or fulfilled our HbA1c based criteria for diabetes in the MHR anytime after their baseline exam in the MDC-CC until June 2007 were classified as having new onset diabetes.

The study protocols were approved by the ethics committee of Lund University. All participants provided written informed consent.

Statistics

SPSS statistical software (version 14.0) was used for all calculations. Group wise differences in continuous variables were tested using student's t-test and reported as means±SD if normally distributed whereas they were tested with Mann-Whitney test and reported as medians and interquartile ranges if not normally distributed. Differences in dichotomous variables were tested using chi-2 test. The P-value for linear trend of fasting glucose and insulin over quartiles P-copeptin in non-diabetic subjects was assessed using linear regression with fasting insulin concentration transformed with the natural logarithm. We used crude and multivariate adjusted logistic regression to test if increasing quartiles of P-copeptin (Q1copeptin-Q4copeptin, Q1copeptin being reference category) were related to diabetes at baseline in the entire cohort (n=4742). In subjects without diabetes at baseline (n=4377), crude and multivariate logistic regression was used to test if increasing quartiles of P-copeptin (Q1copeptin-Q4copeptin, Q1copeptin being reference category) were related to insulin resistance, defined as belonging to the top quartile of fasting insulin, and to new onset diabetes. Finally, the relationship between increasing quartiles of P-copeptin and risk of new onset diabetes was tested in subjects without impaired fasting glucose (fasting plasma glucose 6.1 mmol/L corresponding to FBG<5.5 mmol/L) (n=3702). Data from logistic regression analyses were expressed as odds ratio (OR) and 95% confidence intervals (CI). A two sided P-value of <0.05 was considered statistically significant.

To assess sensitivity and specificity of P-copeptin in predicting new onset diabetes on top of sets of classical diabetes predictors, we compared the area under the Receiver Operating Characteristic (ROC) curves using both a personal model (age, gender, BMI and diabetes heredity) and a clinical model (personal model + systolic blood pressure, triglycerides, HDL, waist circumference and FBG) with and without P-copeptin in each of the two models.

Results

Figure 6:
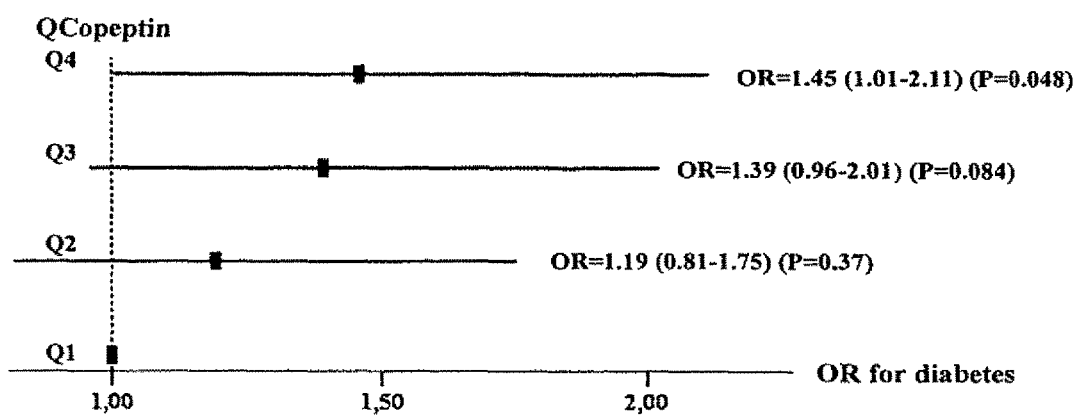
FIG. 6: Elevated plasma copeptin is independently associated with diabetes. Plotted are ORs for diabetes for the quartiles of copeptin levels. Adjusted for: age, sex, triglyceride (TG), HDL, Systolic blood pressure (SBP), diastolic blood pressure (DBP), anti-hypertensive treatment (AHT), body mass index (BMI), waist, waist-hip-ratio (W/H), cystatin C, CRP, previous cardiovascular disease (CVD).
Figure 11:
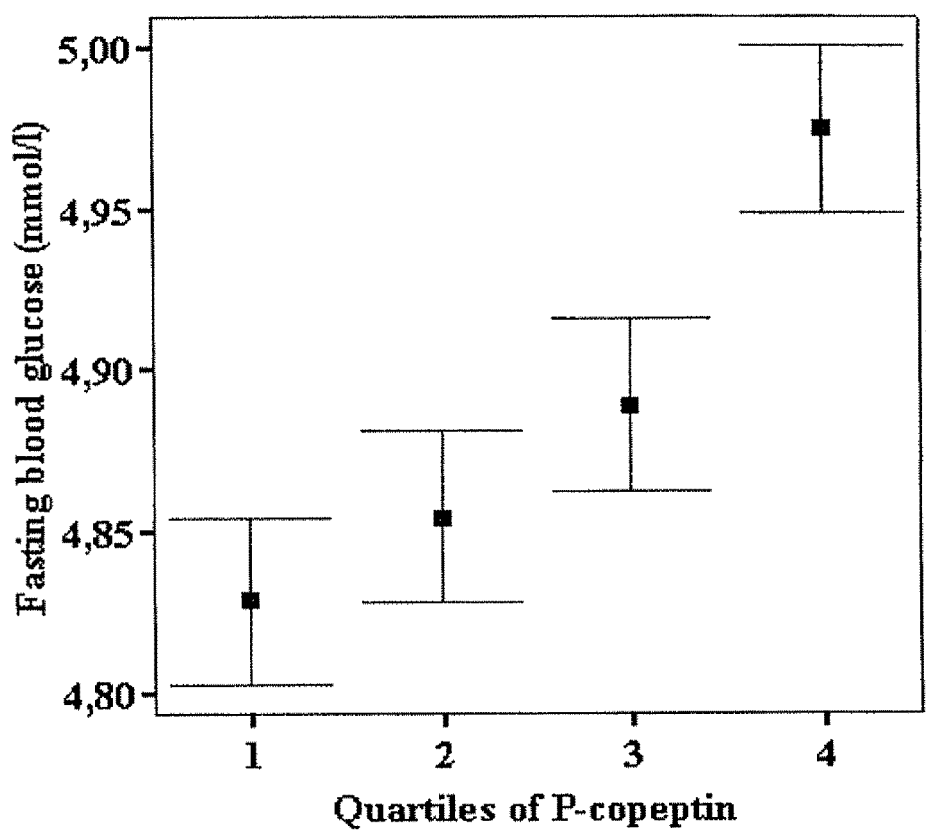
FIG. 11: Fasting blood glucose level (mmol/L) correlated to quartiles of increasing plasma copeptin, expressed as mean with 95% confidence intervals, in non diabetic subjects (n=4377). P (linear trend)<0.001
Figure 12:
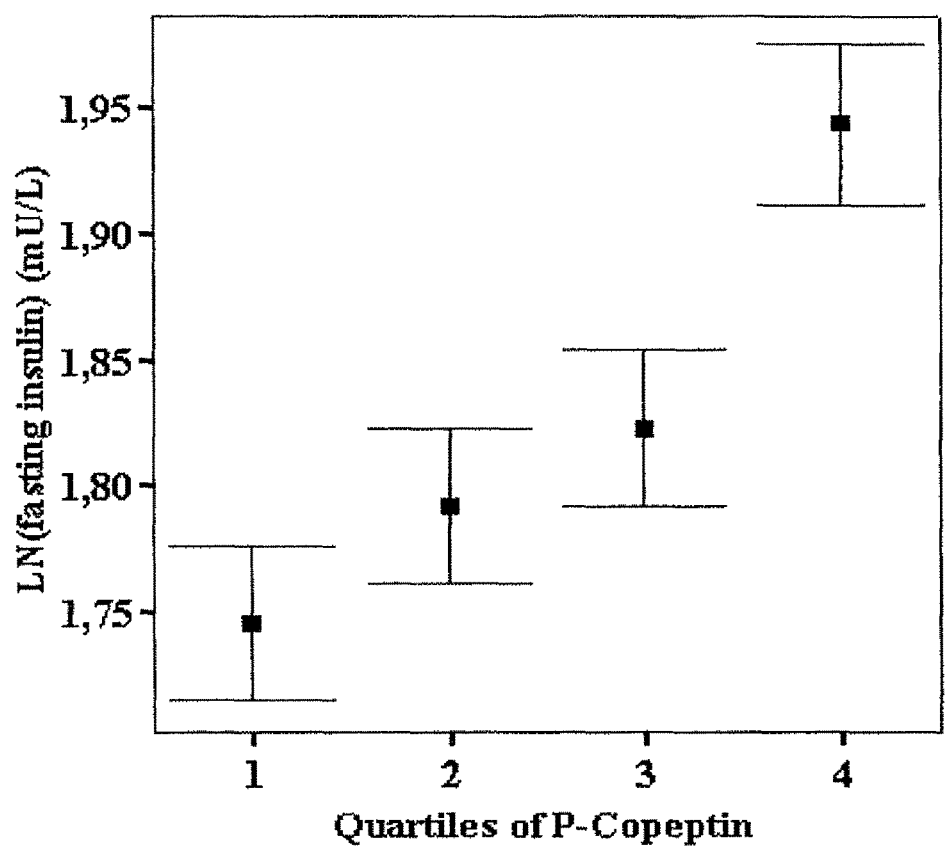
FIG. 12: Fasting insulin glucose level (mU/L) correlated to quartiles of increasing plasma copeptin, expressed as mean with 95% confidence intervals, in non diabetic subjects (n=4377). P (linear trend)<0.001

Of patients with diabetes at the baseline exam (n=365), only 29% reported a history of physician diagnosed diabetes or treatment whereas the majority (71%) were classified as having diabetes based on FBG≥6.1 mmol/L at the baseline exam. P-copeptin was higher among patients with diabetes as compared to non-diabetic subjects (Table 1). In the non-diabetic segment of the population, FBG increased with copeptin (FIG. 11). There was a gradual increase in the OR for diabetes with increasing quartiles of copeptin in both a crude model and after adjustment for all baseline characteristics which significantly differed in univariate comparisons between diabetes patients and controls (Table 1) except for fasting plasma insulin concentration (model 1 adjustment) (Table 2) (FIG. 6). Among non-diabetic subjects, plasma concentration of insulin increased gradually with quartiles of P-copeptin (FIG. 12) and the OR for insulin resistance (top quartile of fasting plasma insulin in the non-diabetic segment of the population) increased with P-copeptin in both crude analysis and after extended model 1 adjustment including model 1 covariates and FBG (Table 2). Among subjects without diabetes at baseline the copeptin concentrations at the quartile borders were as follows: Q1/Q2: 3.13 pmol/L, Q2/Q3: 5.05 pmol/L, Q3/Q4: 7.94 pmol/L.

Figure 7:
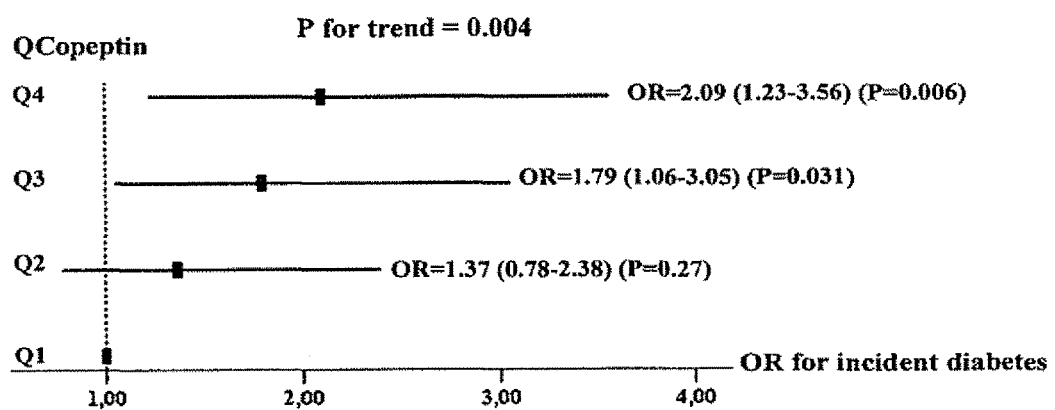
FIG. 7: Elevated plasma copeptin is an independent predictor of future diabetes (subjects with known diabetes or fasting blood glucose (FBG)>6.0 mM at baseline excluded). Effect is independent of baseline glucose. Plotted are ORs for incident diabetes for the quartiles of copeptin levels. Adjusted for: age, sex, TG, HDL, SBP, DBP, AHT, BMI, waist, W/H, cystatin C, CRP, previous CVD, smoking, diabetes heredity, fP-insulin and fB-glucose.
Figure 8:
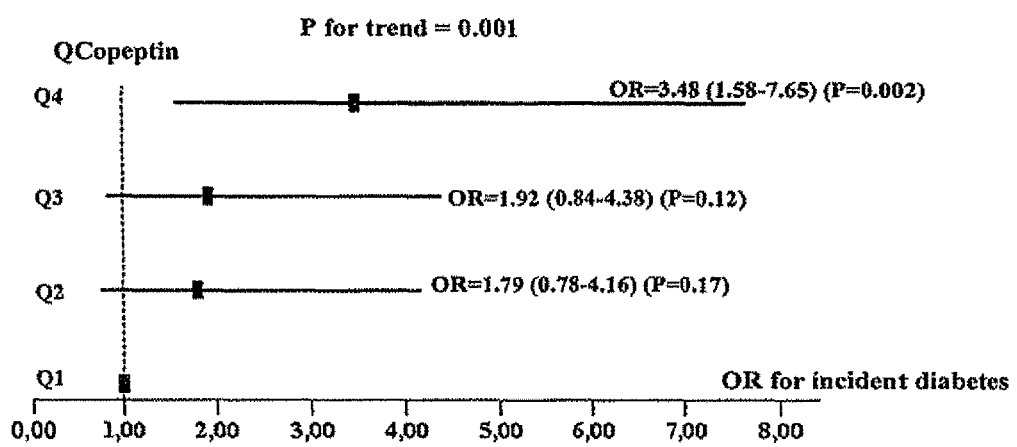
FIG. 8: Elevated plasma copeptin is an independent predictor of future diabetes (subjects with known diabetes or FBG≥5.4 mM at baseline excluded). Effect independent of glucose and remains (strengthens after exclusion of IFG. Plotted are ORs for incident diabetes for the quartiles of copeptin levels. Adjusted for: age, sex, TG, HDL, SBP, DBP, AHT, BMI, waist, W/H, cystatin C, CRP, previous CVD, smoking, diabetes heredity, fP-insulin and fB-glucose.
Figure 9:
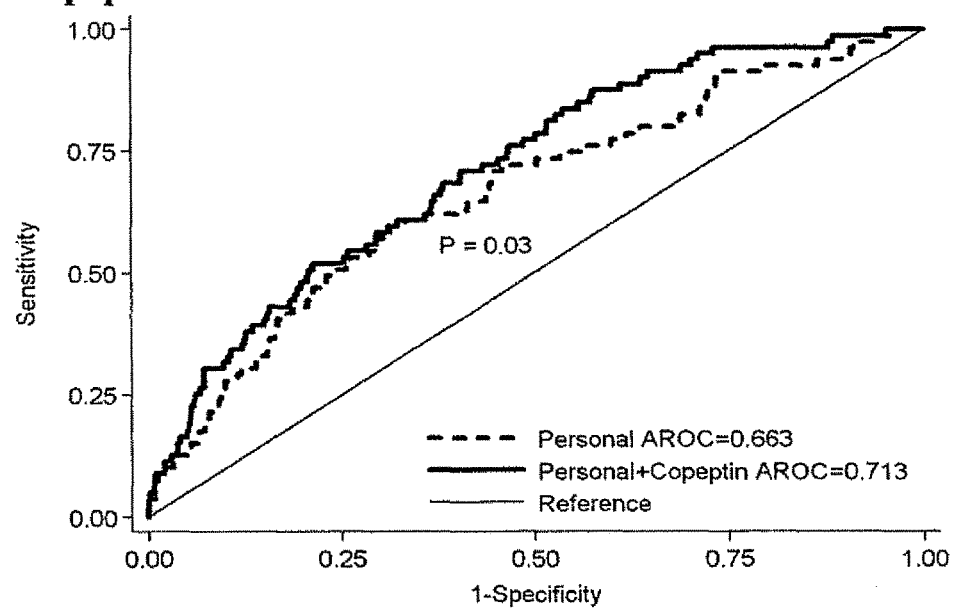
FIG. 9: ROC plots for the prediction of future diabetes using a) a combination of age, sex, BMI and diabetes mellitus (DM) heredity and b) by adding copeptin to this combination.
Figure 10:
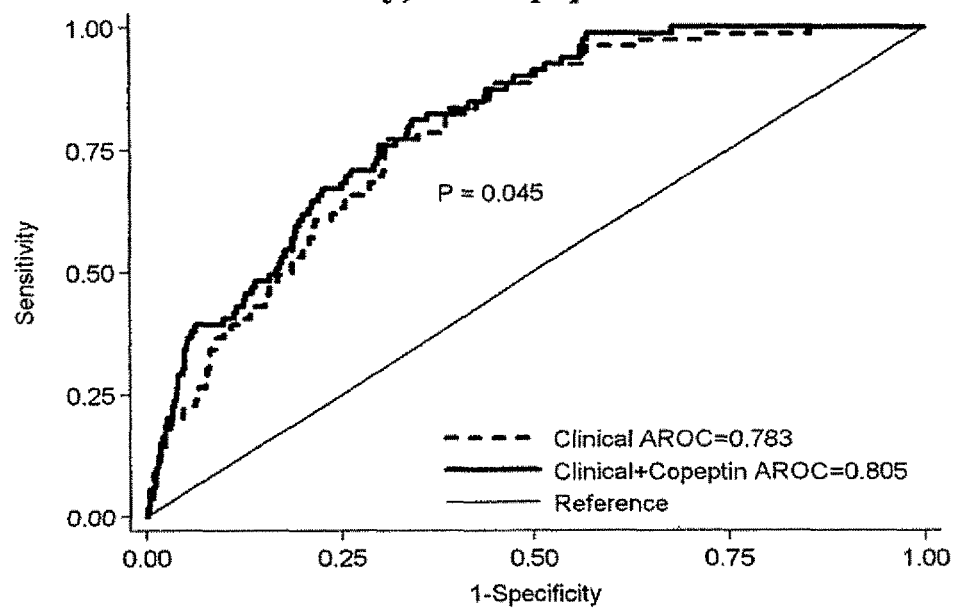
FIG. 10: ROC plots for the prediction of future diabetes using a) a combination of age, sex, SBP, BMI, waist, glucose, TG, HDL and DM heredity and b) by adding copeptin to this combination.

Among subjects without diabetes at baseline (n=4377), 174 subjects developed new onset diabetes and among subjects free from impaired fasting glucose at baseline (n=3702), 79 subjects developed new onset diabetes during follow-up (Table 3). P-copeptin at baseline was significantly higher in subjects who developed new onset diabetes compared with those who did not both among subjects without diabetes at baseline and among subjects without impaired fasting glucose at baseline (Table 3). The likelihood of developing new onset diabetes increased with P-copeptin quartiles in crude analysis as well as after adjustment for model 1 covariates and fasting insulin, FBG, smoking, diabetes heredity and LDL both in subjects without diabetes (FIG. 7) and in subjects without impaired fasting glucose at baseline (FIG. 8) (Table 4). In subjects without diabetes at baseline, the area under the Receiver Operating Characteristic (ROC) curve for the prediction of future diabetes increased from 69.4 to 71.0% (P=0.08) and from 83.2 to 84.1% (P=0.007) when copeptin was added to the personal model and clinical model of diabetes prediction, respectively. In subjects without impaired fasting glucose at baseline, the area under the ROC curve for the prediction of future diabetes increased from 66.3 to 71.3% (P=0.03) (FIG. 9) and from 78.3 to 80.5% (P=0.04) (FIG. 10) when copeptin was added to the personal model and clinical model of diabetes prediction, respectively.

Discussion

Here we demonstrate in a large population based cohort that P-copeptin is markedly elevated in diabetes patients and that P-copeptin increases linearly with FBG in non-diabetic subjects, i.e. in subjects with FBG levels that definitely do not affect osmolality. In non-diabetic subjects there was a strong cross sectional relationship between P-copeptin and insulin resistance (as estimated by fasting plasma insulin) and this relationship was independent of a large number of confounding factors, including FBG. Moreover, P-copeptin at baseline was a strong risk factor for development of new onset diabetes during follow-up. Importantly, this relationship was independent of a broad range of well known risk factors for diabetes at baseline, including FBG and fasting insulin, the latter two of which were strongly cross sectionally related to P-copeptin. When the cohort was restricted to subjects without impaired fasting glucose the relationship between P-copeptin and new onset diabetes was strengthened despite the fact almost half of the new onset diabetes cases occurred among subjects who had impaired fasting glucose at baseline. As expected, FBG was the strongest risk factor for new onset diabetes. Each 1 mmol/L increase of FBG at baseline increased the risk of future diabetes with an OR of 11.4 (95% CI 7.4-17.5) in the fully adjusted model (Table 4). Baring this in mind, it is impressive that the top versus bottom quartile of copeptin was associated with an OR of 3.6 for new onset diabetes in subjects without impaired fasting glucose after full adjustment of baseline covariates including FBG (Table 4). Importantly, in subjects without impaired fasting glucose, there was a significant 2.2-4.0% improvement of the area under the ROC curve when P-copeptin was added to models of classical diabetes risk factors, indicating that P-copeptin improves sensitivity and specificity of individual risk prediction of diabetes. In the larger sample, including subjects with impaired fasting glucose, P-copeptin improved the area under the ROC curve less markedly. The lesser improvement of the area under the ROC curve in analyses including subjects with higher levels of FBG (i.e. subjects with impaired fasting glucose) may result from FBG being a more powerful predictor of diabetes at FBG levels near the diagnostic limit of 6.1 mmol/L, whereas markers that are not diagnostic for diabetes, such as P-copeptin, may better signal diabetes susceptibility earlier in the pre-diabetic state. Importantly, novel risk markers as screening tools for future diabetes risk are more important in subjects with normal FBG as subjects with impaired fasting glucose commonly get medical attention aimed at predicting diabetes anyway, given the well known strong diabetes predictive value of an elevated FBG. Thus, our findings indicate that there may be clinical value in adding P-copeptin to established screening tools for prediction of diabetes. We do not have data on subtypes of new onset diabetes, however, given the mean age of 57 years in the non-diabetic segment of our population and the strong cross sectional relationship between P-copeptin and insulin resistance, we assume that elevation of P-copeptin indicates risk of type 2 diabetes rather than type 1 diabetes.

Apart from having implications for diabetes prediction, our findings suggest a role of the AVP system in the pathophysiology of diabetes and potentially for development of novel antidiabetic treatment regimens. Animal studies have shown that mice lacking the V1aR (V1aR −/−) display elevated levels of AVP, glucose intolerance and insulin resistance whereas mice lacking the V1bR (V1bR −/−) get the opposite phenotype of lower FBG and improved insulin sensitivity. Based on these animal data and our own findings that elevated P-copeptin is associated with elevated FBG, insulin resistance and increased risk of future diabetes, it can be speculated that elevated AVP, as a consequence of AVP resistance at the level of the V1aR or elsewhere, contributes to insulin resistance and diabetes through stimulation of the V1bR. In fact, pharmacological blockade of the V2R, a potent stimulus of increased AVP secretion through negative feedback on the hypothalamic-neuropituitary axis, was associated with a five-fold increase in hyperglycaemic events during 30 days of tolvaptane treatment in patients with hyponatremia. Thus elevation in AVP, whatever the underlying mechanism is, may contribute to impaired glucose homeostasis, possibly through stimulation of the V1bR. These findings warrant studies on pharmacological manipulations of the AVP system in relation to glucose metabolism in man.

The number of new onset diabetes cases in the MDC-CC may seem lower than expected. There are three important reasons which are the most likely to explain this. (1) The participation rate in the MDC study was only 40% and as a consequence of that, the MDC population is healthier and includes disproportionally many women compared to the background population (Manjer 2001). As a result of this, the relationship between P-copeptin and new onset diabetes that we describe are likely to be underestimated. (2) The diabetes incidence we observe in the three registers are based on the prerequisite that people actively seek health care and not on population screening of glucose levels, leading to lower incidence than observed in studies regularly screening for diabetes by measuring FBG. Furthermore, in contrast to our definition of new onset diabetes, the definition of diabetes at the baseline exam of MDC-CC included measurement of FBG. In fact, of those who were defined as having diabetes at 71% did not report a history of diabetes or antidiabetic treatment but were diagnosed solely based on FBG. Exclusion of this large number of diabetes patients, who were unaware that they had diabetes before the baseline exam, has further markedly decreased the incidence of new onset diabetes during follow-up. (3) Despite the issues discussed above, our study is likely to have missed a number of new onset cases who were in fact diagnosed with diabetes within the health care system. The MHR recorded all HbA1c values in the greater Malmö area from 1990 and onwards, however, we missed cases diagnosed with diabetes in the greater Malmö area without HbA1c being measured or if HbA1c was only measured once or if it was only marginally elevated on repeated occasions. New onset diabetes cases not detected in the MHR as a result of moving outside the greater Malmö area after the MDC-CC baseline exam, would have a reasonable chance to be detected by the nation wide NDR and/or the regional Diabetes 2000 registry, in particular by the NDR as this register was estimated to cover 50% of all diabetes patients in Sweden in 2007. Still, the coverage of the NDR and Diabetes 2000 registers is incomplete. For these reasons, we have classified an unknown number of subjects who did in fact develop diabetes during follow-up as non-diabetics. On the other hand, given the strict HbA1c criteria for new onset diabetes in the MHR and the proven validity of the NDR and Diabetes 2000 register, we are confident on the validity of the endpoint in those subjects whom we did classify as new onset diabetes cases. The validity of the register based new onset diabetes diagnosis is further supported by the fact that most of the well-known risk factors for diabetes were markedly elevated at the MDC-CC baseline in these subjects as compared to those who did not develop diabetes according to the three registers (Table 3). Importantly, these differences were equally pronounced when the study population was restricted to subjects without impaired fasting glucose at baseline excluding the possibility that our findings regarding established diabetes risk factors and P-copeptin in relation to new onset diabetes were solely driven by subjects who had almost diabetic FBG at the MDC-CC baseline exam.

In conclusion, P-copeptin predicts diabetes independently of a broad range of established diabetes risk factors, including fasting levels of glucose and insulin. Our findings suggest a role of the AVP system in diabetes development and may have implications for risk assessment and novel anti-diabetic pharmacotherapy.

TABLE 1

Baseline characteristics of subjects with and without diabetes

| | Non-diabetic subjects (n = 4377) | Diabetes patients (n = 365) | P-value |
|---|---|---|---|
| Age (years) | 57.4 ± 5.9 | 59.5 ± 5.5 | <0.001 |
| FBG (mmol/l) | 4.9 ± 0.45 | 8.1 ± 3.0 | <0.001 |
| Triglycerides (mmol/l)* | 1.12 (0.85-1.53) | 1.64 (1.13-2.33) | <0.001 |
| Systolic BP (mmHg) | 140 ± 19 | 150 ± 20 | <0.001 |
| Diastolic BP (mmHg) | 87 ± 9.4 | 90 ± 9.5 | <0.001 |
| BMI (kg/m2) | 25.5 ± 3.7 | 28.7 ± 4.5 | <0.001 |
| Waist (cm) | 82.6 ± 12 | 94.4 ± 13 | <0.001 |
| Waist-hip-ratio | 0.84 ± 0.09 | 0.91 ± 0.09 | <0.001 |
| HDL (mmol/l) | 1.40 ± 0.37 | 1.23 ± 0.35 | <0.001 |
| LDL (mmol/l) | 4.2 ± 0.98 | 4.2 ± 1.0 | 0.22 |
| Cystatin C (mg/l) | 0.773 ± 0.143 | 0.809 ± 0.193 | 0.001 |
| Copeptin (pmol/l)* | 5.04 (3.12-7.94) | 6.90 (4.32-10.7) | <0.001 |
| Insulin (mU/L)* | 6.0 (4.0-9.0) | 12 (7.0-18) | <0.001 |
| CRP (mg/l) | 1.3 (0.6-2.6) | 2.3 (1.3-4.5) | <0.001 |
| Men (%) | 39.2 | 56.2 | <0.001 |
| AHT (%) | 14.7 | 37.3 | <0.001 |
| Current smoker (%) | 26.5 | 24.4 | 0.41 |
| Diabetes heredity (%) | 3.0 | 3.0 | 0.87 |
| Previous CVD (%) | 2.0 | 3.8 | 0.02 |

Continuous variables are given as means ± SD unless otherwise specified
*median (interquartile range)
AHT, anti-hypertensive treatment; BMI, Body-mass-index; FBG, fasting blood glucose; previous CVD, cardiovascular disease present before baseline examination.

TABLE 2

Prevalent diabetes and insulin resistance in relation to quartiles of baseline P-copeptin.

| Dependent variable | | OR (95% CI) Q2 copeptin vs Q1 copeptin | OR (95% CI) Q3 copeptin vs Q1 copeptin | OR (95% CI) Q4 copeptin vs Q1 copeptin | P for linear trend |
|---|---|---|---|---|---|
| Diabetes* | crude | 1.44 (1.00-2.07) | 1.92 (1.36-2.71) | 2.83 (2.04-3.93) | <0.001 |
| | Adjusted | 1.19 (0.81-1.75) | 1.39 (0.96-2.01) | 1.45 (1.00-2.11) | 0.04 |
| Hyper-insulinemia† | crude | 1.30 (1.06-1.60) | 1.53 (1.25-1.87) | 2.34 (1.93-2.85) | <0.001 |
| | Adjusted | 1.19 (0.94-1.51)2 | 1.26 (0.99-1.60)2 | 1.61, 1.26-2.06)2 | <0.001 |

*Analysis of diabetes prevalence (n = 365) in the entire cohort (n = 4742)
†Analysis of hyperinsulinemia (highest quartile of fasting plasma insulin concentration among non-diabetic subjects) among non-diabetic subjects (n = 4377)
‡Adjusted for age, sex, HDL, triglycerides, blood pressure, antihypertensive treatment, body mass index, waist, waist/hip ratio, cystatin C, CRP and prevalent cardiovascular disease (model 1)
§Adjusted for model 1 and FBG.

TABLE 3

Baseline characteristics in subjects who did and did not convert to diabetes during follow-up Subjects without diabetes at baseline (n = 4377)

| | Non-converters (n = 4203) | Incident diabetes (n = 174) | P |
|---|---|---|---|
| Age (years) | 57.3 ± 5.9 | 57.9 ± 5.7 | 0.26 |
| Men (%) | 38.9 | 45.4 | 0.09 |
| Glucose (mmol/l) | 4.9 ± 0.44 | 5.4 ± 0.44 | <0.001 |
| Triglycerides (mmol/l) | 1.11 (0.84-1.51) | 1.46 (1.05-1.96) | <0.001 |
| Systolic BP (mmHg) | 140 ± 19 | 146 ± 19 | <0.001 |
| Diastolic BP (mmHg) | 86 ± 9.3 | 90 ± 10 | <0.001 |
| AHT (%) | 14.2 | 27.6 | <0.001 |
| BMI (kg/m2) | 25.4 ± 3.6 | 28.2 ± 4.7 | <0.001 |
| Waist (cm) | 82.2 ± 12 | 91.5 ± 14 | <0.001 |
| Waist-hip-ratio | 0.84 ± 0.09 | 0.89 ± 0.10 | <0.001 |
| HDL (mmol/l) | 1.41 ± 0.37 | 1.25 ± 0.33 | <0.001 |
| LDL (mmol/l) | 4.2 ± 0.98 | 4.3 ± 1.0 | 0.06 |
| Cystatin C (mg/l) | 0.77 ± 0.14 | 0.82 ± 0.21 | <0.001 |
| Copeptin (pmol/l) | 4.98 (3.09-7.84) | 6.35 (4.05-9.88) | <0.001 |
| Insulin (mU/L) | 6.0 (4.0-9.0) | 9.0 (6.0-13) | <0.001 |
| CRP (mg/l) | 1.2 (0.6-2.6) | 2.1 (0.9-4.1) | <0.001 |
| Current smoker (%) | 26.4 | 29.5 | 0.37 |
| Diabetes heredity (%) | 2.8 | 6.9 | 0.002 |
| Previous CVD (%) | 2.0 | 2.3 | 0.80 |

Subjects without impaired fasting glucose at baseline (n = 3702)

| | Non-converters (n = 3623) | Incident diabetes (n = 79) | P |
|---|---|---|---|
| Age (years) | 57.2 ± 5.9 | 58.1 ± 5.4 | 0.20 |
| Men (%) | 36.5 | 38.0 | 0.79 |
| Glucose (mmol/l) | 4.7 ± 0.34 | 5.0 ± 0.28 | <0.001 |
| Triglycerides (mmol/l) | 1.34 (0.82-1.47) | 1.34 (1.06-1.92) | <0.001 |
| Systolic BP (mmHg) | 139 ± 19 | 146 ± 19 | 0.001 |
| Diastolic BP (mmHg) | 86 ± 9.2 | 89 ± 9.5 | 0.004 |
| AHT (%) | 13.4 | 24.1 | 0.006 |
| BMI (kg/m2) | 25.2 ± 3.6 | 27.5 ± 4.9 | <0.001 |
| Waist (cm) | 81.3 ± 12 | 88.7 ± 14 | <0.001 |
| Waist-hip-ratio | 0.84 ± 0.09 | 0.87 ± 0.09 | <0.001 |
| HDL (mmol/l) | 1.43 ± 0.37 | 1.27 ± 0.32 | <0.001 |
| LDL (mmol/l) | 4.2 ± 0.98 | 4.1 ± 0.93 | 0.99 |
| Cystatin C (mg/l) | 0.77 ± 0.14 | 0.83 ± 0.27 | <0.001 |
| Copeptin (pmol/l) | 4.90 (3.03-7.65) | 6.74 (4.44-10.9) | 0.001 |
| Insulin (mU/L) | 6.0 (4.0-8.0) | 8.0 (6.0-11) | <0.001 |
| CRP (mg/l) | 1.2 (0.6-2.4) | 2.4 (1.0-4.1) | <0.001 |
| Current smoker (%) | 25.4 | 30.4 | 0.31 |
| Diabetes heredity (%) | 3.0 | 7.6 | 0.02 |
| Previous CVD (%) | 1.9 | 2.5 | 0.67 |

Continuous variables are given as means ± SD unless otherwise specified
*median (interquartile range)
AHT, anti-hypertensive treatment; BMI, Body-mass-index; FBG, fasting blood glucose; previous CVD, cardiovascular disease present before baseline examination.

TABLE 4

New onset diabetes in relation to quartiles of baseline P-copeptin.

| Dependent variable | | OR (95% CI) Q2 copeptin vs Q1 copeptin | OR (95% CI) Q3 copeptin vs Q1 copeptin | OR (95% CI) Q4 copeptin vs Q1 copeptin | P (test for linear trend) |
|---|---|---|---|---|---|
| Incident diabetes among non-DM* | crude | 1.28 (0.76-2.15) | 1.94 (1.19-3.14) | 2.64 (1.66-4.19) | <0.001 |
|  | adjusted‡ | 1.37 (0.78-2.39) | 1.79 (1.06-3.05) | 2.09 (1.23-3.56) | 0.004 |
| Incident diabetes among non-IFG† | crude | 1.85 (0.81-4.20) | 2.12 (0.95-4.73) | 4.56 (2.18-9.52) | <0.001 |
|  | adjusted‡ | 1.80 (0.78-4.16) | 1.92 (0.84-4.38) | 3.48 (1.58-7.65) | 0.001 |

*Subjects who developed diabetes during follow-up (n = 174) among subjects without diabetes at baseline (n = 4377)
†Subjects who developed diabetes during follow-up (n = 79) among subjects without impaired fasting glucose at baseline (n = 3702)
‡Adjusted for age, sex, HDL, triglycerides, blood pressure, antihypertensive treatment, body mass index, waist, waist/hip ratio, cystatin C, CRP and prevalent cardiovascular disease, smoking, diabetes heredity, LDL, FBG and fasting insulin.

The invention claimed is:

1. A method for diagnosing metabolic syndrome in a subject comprising:
   a. detecting and quantitating the level of arginine vasopressin pro-hormone copeptin fragment in a sample from said patient,
      wherein said detection and quantitation comprises contacting the sample with a diagnostic assay reagent comprising at least one monoclonal antibody or fragment thereof that specifically binds to the arginine vasopressin pro-hormone copeptin fragment at the epitope corresponding to amino acids 132-147 of pre-pro-vasopressin of SEQ ID NO: 1, and detecting and quantitating thus-formed complexes of the antibody or fragment thereof and arginine vasopressin pro-hormone copeptin fragment,
   b. detecting and quantitating at least one other clinical and/or laboratory parameter associated with the diagnosis of metabolic syndrome, and
   c. correlating the level of the arginine vasopressin pro-hormone copeptin fragment in conjunction with the at least one other clinical and/or laboratory parameter associated with the diagnosis of metabolic syndrome, with the diagnosis of metabolic syndrome.

2. An assay for the determination of the copeptin level in a sample, wherein the assay has a total assay imprecision of 20% Coefficient of Variation (CV) at a copeptin concentration below 2.2 pmol/L and a lower than 20% CV at normal range-concentrations above that concentration, and/or 10% CV at a concentration below 9 pmol/l and a lower than 10% CV at normal range-concentrations above that concentration,
wherein the assay comprises two anti-copeptin antibodies, and
wherein at least one of the antibodies is a monoclonal antibody or fragment thereof that binds to an epitope comprising amino acids 132-147 of pre-pro-vasopressin of SEQ ID NO: 1.

3. An assay of claim 2 for the determination of the copeptin level in a sample, wherein the assay has a total assay imprecision of maximally 12% at the median Copeptin concentration determined in serum or plasma of a Caucasian population of healthy fasting females at rest.

4. An assay for the determination of the copeptin level in a sample, wherein the assay comprises two anti-copeptin antibodies, wherein at least one of the antibodies is a monoclonal antibody or fragment thereof that binds to an epitope comprising amino acids 132-147 of pre-pro-vasopressin of SEQ ID NO: 1.

5. A method according to claim 1, wherein the diagnosis of metabolic syndrome comprises predicting the risk of a subject for developing diabetes mellitus.

6. The method of claim 1, wherein the correlation comprises comparing the level of arginine vasopressin pro-hormone copeptin fragment in conjunction with said at least one other clinical and/or laboratory parameter in the patient, to the level of arginine vasopressin pro-hormone copeptin fragment in conjunction with said at least one other clinical and/or laboratory parameter in an ensemble of pre-determined samples in a population of comparable subjects who have metabolic syndrome or do not have metabolic syndrome, wherein said diagnosis is based on a statistically significant correlation of the level of the arginine vasopressin pro-hormone copeptin fragment in conjunction with said at least one other clinical and/or laboratory parameter in the patient sample with the levels of the arginine vasopressin pro-hormone copeptin fragment in conjunction with said said at least one other clinical and/or laboratory parameter in the pre-determined samples.

7. The assay of claim 6, wherein the assay has a total assay imprecision of 20% CV at a copeptin concentration below 2.2 pmol/L.

* * * * *

```
                          SEQUENCE LISTING

<160> NUMBER OF SEQ ID NOS: 3

<210> SEQ ID NO 1
<211> LENGTH: 164
<212> TYPE: PRT
<213> ORGANISM: Homo sapiens

<400> SEQUENCE: 1

Met Pro Asp Thr Met Leu Pro Ala Cys Phe Leu Gly Leu Leu Ala Phe
1               5                   10                  15

Ser Ser Ala Cys Tyr Phe Gln Asn Cys Pro Arg Gly Gly Lys Arg Ala
            20                  25                  30

Met Ser Asp Leu Glu Leu Arg Gln Cys Leu Pro Cys Gly Pro Gly Gly
        35                  40                  45

Lys Gly Arg Cys Phe Gly Pro Ser Ile Cys Cys Ala Asp Glu Leu Gly
    50                  55                  60

Cys Phe Val Gly Thr Ala Glu Ala Leu Arg Cys Gln Glu Glu Asn Tyr
65                  70                  75                  80

Leu Pro Ser Pro Cys Gln Ser Gly Gln Lys Ala Cys Gly Ser Gly Gly
                85                  90                  95

Arg Cys Ala Ala Phe Gly Val Cys Cys Asn Asp Glu Ser Cys Val Thr
            100                 105                 110

Glu Pro Glu Cys Arg Glu Gly Phe His Arg Arg Ala Arg Ala Ser Asp
        115                 120                 125

Arg Ser Asn Ala Thr Gln Leu Asp Gly Pro Ala Gly Ala Leu Leu Leu
    130                 135                 140

Arg Leu Val Gln Leu Ala Gly Ala Pro Glu Pro Phe Glu Pro Ala Gln
145                 150                 155                 160

Pro Asp Ala Tyr

<210> SEQ ID NO 2
<211> LENGTH: 39
<212> TYPE: PRT
<213> ORGANISM: Homo sapiens

<400> SEQUENCE: 2

Ala Ser Asp Arg Ser Asn Ala Thr Gln Leu Asp Gly Pro Ala Gly Ala
1               5                   10                  15

Leu Leu Leu Arg Leu Val Gln Leu Ala Gly Ala Pro Glu Pro Phe Glu
            20                  25                  30
```

```
Pro Ala Gln Pro Asp Ala Tyr
        35

<210> SEQ ID NO 3
<211> LENGTH: 145
<212> TYPE: PRT
<213> ORGANISM: Homo sapiens

<400> SEQUENCE: 3

Cys Tyr Phe Gln Asn Cys Pro Arg Gly Lys Arg Ala Met Ser Asp
1               5                   10                  15

Leu Glu Leu Arg Gln Cys Leu Pro Cys Gly Pro Gly Gly Lys Gly Arg
            20                  25                  30

Cys Phe Gly Pro Ser Ile Cys Cys Ala Asp Glu Leu Gly Cys Phe Val
            35                  40                  45

Gly Thr Ala Glu Ala Leu Arg Cys Gln Glu Glu Asn Tyr Leu Pro Ser
        50                  55                  60

Pro Cys Gln Ser Gly Gln Lys Ala Cys Gly Ser Gly Gly Arg Cys Ala
65                  70                  75                  80

Ala Phe Gly Val Cys Cys Asn Asp Glu Ser Cys Val Thr Glu Pro Glu
                85                  90                  95

Cys Arg Glu Gly Phe His Arg Arg Ala Arg Ala Ser Asp Arg Ser Asn
                100                 105                 110

Ala Thr Gln Leu Asp Gly Pro Ala Gly Ala Leu Leu Leu Arg Leu Val
            115                 120                 125

Gln Leu Ala Gly Ala Pro Glu Pro Phe Glu Pro Ala Gln Pro Asp Ala
        130                 135                 140

Tyr
145
```